United States Patent
Barnes et al.

(10) Patent No.: US 9,750,639 B2
(45) Date of Patent: Sep. 5, 2017

(54) DISPOSABLE VITRECTOMY HANDPIECE

(71) Applicant: DOHENY EYE INSTITUTE, Los Angeles, CA (US)

(72) Inventors: Aaron Barnes, Los Angeles, CA (US); Charles DeBoer, Pasadena, CA (US); Matthew McCormick, Forest Falls, CA (US)

(73) Assignee: Doheny Eye Institute, Los Angeles, CA (US)

( * ) Notice: Subject to any disclaimer, the term of this patent is extended or adjusted under 35 U.S.C. 154(b) by 392 days.

(21) Appl. No.: 14/256,726

(22) Filed: Apr. 18, 2014

(65) Prior Publication Data

US 2014/0296900 A1    Oct. 2, 2014

Related U.S. Application Data (63) Continuation of application No. 11/963,749, filed on Dec. 21, 2007, now abandoned.

(60) Provisional application No. 60/876,796, filed on Dec. 21, 2006.

(51) Int. Cl.
    *A61B 17/32*      (2006.01)
    *A61F 9/007*      (2006.01)
    *A61B 17/00*      (2006.01)

(52) U.S. Cl.
    CPC .. *A61F 9/00763* (2013.01); *A61B 17/320016* (2013.01); *A61B 2017/0023* (2013.01); *A61B 2017/00477* (2013.01)

(58) Field of Classification Search
    CPC ................ A61F 9/007; A61F 9/00763; A61B 2017/0023; A61B 2017/00477; A61B 17/32; A61B 17/320016
    See application file for complete search history.

(56) References Cited

U.S. PATENT DOCUMENTS

| | | |
|---|---|---|
| 3,732,858 A | 5/1973 | Banko |
| 3,882,872 A | 5/1975 | Douvas et al. |
| 3,937,222 A | 2/1976 | Banko |
| 3,976,077 A | 8/1976 | Kerfoot, Jr. |
| 3,990,453 A | 11/1976 | Douvas et al. |

(Continued)

FOREIGN PATENT DOCUMENTS

| | | |
|---|---|---|
| EP | 0 310 285 A2 | 4/1989 |
| JP | 2002-177317 | 6/2002 |

(Continued)

OTHER PUBLICATIONS

Extended European Search Report dated May 24, 2011 in European Application No. 07865997.6.

(Continued)

*Primary Examiner* — Victor Nguyen
(74) *Attorney, Agent, or Firm* — Baker Botts L.L.P.

(57) ABSTRACT

Electric vitrectomy handpieces are provided. The handpiece includes a motor, a clutch mechanism, an oscillating drive mechanism, a cutting tip and a handle. The motor is attached to the clutch, and the clutch is attached to the oscillating drive mechanism. When the motor is operational, the clutch expands to engage the oscillating drive mechanism and the oscillating drive mechanism converts the rotational motion of the clutch to the reciprocating motion of the cutting tip. When the motor is at rest, the clutch retracts to allow aspiration.

16 Claims, 6 Drawing Sheets

(56) References Cited

U.S. PATENT DOCUMENTS

| | | |
|---|---|---|
| 4,167,944 A | 9/1979 | Banko |
| 4,368,734 A | 1/1983 | Banko |
| 4,428,748 A | 1/1984 | Peyman et al. |
| 4,508,532 A | 4/1985 | Drews et al. |
| 4,530,356 A | 7/1985 | Helfgott et al. |
| 4,598,710 A | 7/1986 | Kleinberg et al. |
| 4,662,869 A | 5/1987 | Wright |
| 4,757,814 A | 7/1988 | Wang et al. |
| 4,811,734 A | 3/1989 | McGurk-Burleson et al. |
| 4,844,064 A | 7/1989 | Thimsen et al. |
| 4,850,354 A | 7/1989 | McGurk-Burleson et al. |
| 4,867,157 A | 9/1989 | McGurk-Burleson et al. |
| 4,895,166 A | 1/1990 | Farr et al. |
| 4,908,015 A | 3/1990 | Anis |
| 4,909,249 A | 3/1990 | Akkas et al. |
| 4,911,161 A | 3/1990 | Schechter |
| 4,940,468 A | 7/1990 | Petillo |
| 4,983,179 A | 1/1991 | Sjostrom |
| 4,986,827 A | 1/1991 | Akkas et al. |
| 5,047,008 A | 9/1991 | De Juan, Jr. et al. |
| 5,084,052 A | 1/1992 | Jacobs |
| 5,106,364 A | 4/1992 | Hayafuji et al. |
| 5,112,339 A | 5/1992 | Zelman |
| 5,139,504 A | 8/1992 | Zelman |
| 5,346,497 A | 9/1994 | Simon et al. |
| 5,391,180 A | 2/1995 | Tovey et al. |
| 5,403,276 A | 4/1995 | Schechter et al. |
| 5,423,844 A | 6/1995 | Miller |
| 5,437,630 A | 8/1995 | Daniel et al. |
| 5,464,389 A | 11/1995 | Stahl |
| 5,492,528 A | 2/1996 | Anis |
| 5,562,691 A | 10/1996 | Tano et al. |
| 5,613,972 A | 3/1997 | Lee et al. |
| 5,630,827 A | 5/1997 | Vijfvinkel |
| 5,690,660 A | 11/1997 | Kauker et al. |
| 5,722,945 A | 3/1998 | Anis et al. |
| 5,730,718 A | 3/1998 | Anis et al. |
| 5,746,713 A | 5/1998 | Hood et al. |
| 5,766,194 A | 6/1998 | Smith |
| 5,792,167 A | 8/1998 | Kablik et al. |
| 5,807,401 A | 9/1998 | Grieshaber et al. |
| 5,827,292 A | 10/1998 | Anis |
| 5,843,111 A | 12/1998 | Vijfvinkel |
| 5,911,699 A | 6/1999 | Anis et al. |
| 6,007,513 A | 12/1999 | Anis et al. |
| 6,007,556 A | 12/1999 | Kablik et al. |
| 6,027,514 A | 2/2000 | Stine et al. |
| 6,203,518 B1 | 3/2001 | Anis et al. |
| 6,217,543 B1 | 4/2001 | Anis et al. |
| 6,258,111 B1 * | 7/2001 | Ross ............... A61B 17/32002 606/171 |
| 6,342,061 B1 | 1/2002 | Kauker et al. |
| 6,352,519 B1 | 3/2002 | Anis et al. |
| 6,488,695 B1 | 12/2002 | Hickingbotham |
| 6,514,268 B2 | 2/2003 | Finlay et al. |
| 6,540,695 B1 | 4/2003 | Burbank et al. |
| 6,629,986 B1 | 10/2003 | Ross et al. |
| 6,638,235 B2 | 10/2003 | Miller et al. |
| 6,730,106 B2 | 5/2004 | Kanda et al. |
| 6,773,445 B2 | 8/2004 | Finlay et al. |
| 7,013,566 B1 | 3/2006 | Bellm et al. |
| 7,083,608 B2 | 8/2006 | Tomita et al. |
| 7,276,032 B2 | 10/2007 | Hibner |
| 7,470,277 B2 | 12/2008 | Finlay et al. |
| 7,758,537 B1 | 7/2010 | Brunell et al. |
| 8,172,865 B2 | 5/2012 | DeBoer et al. |
| 2002/0052617 A1 | 5/2002 | Anis et al. |
| 2003/0060841 A1 | 3/2003 | Del Rio et al. |
| 2003/0144606 A1 | 7/2003 | Kadziauskas et al. |
| 2004/0049217 A1 | 3/2004 | Ross et al. |
| 2004/0158236 A1 | 8/2004 | Thyzel |
| 2005/0256512 A1 | 11/2005 | Del Rio et al. |
| 2006/0036270 A1 | 2/2006 | Terao |
| 2006/0281599 A1 | 12/2006 | Murakami et al. |
| 2007/0088376 A1 | 4/2007 | Zacharias |
| 2007/0129732 A1 | 6/2007 | Zacharias |
| 2007/0185512 A1 | 8/2007 | Kirchhevel |
| 2007/0185514 A1 | 8/2007 | Kirchhevel |
| 2007/0191758 A1 | 8/2007 | Hunter et al. |
| 2008/0146965 A1 | 6/2008 | Privitera et al. |
| 2008/0149197 A1 | 6/2008 | Turner et al. |
| 2008/0172078 A1 | 7/2008 | Svetic |
| 2008/0188881 A1 | 8/2008 | Chon |
| 2008/0208233 A1 | 8/2008 | Barnes et al. |
| 2009/0082715 A1 | 3/2009 | Charles |
| 2009/0287233 A1 | 11/2009 | Huculak |

FOREIGN PATENT DOCUMENTS

| | | |
|---|---|---|
| JP | 2006-015984 | 1/2006 |
| WO | WO9305718 | 4/1993 |
| WO | WO 98/52502 | 11/1998 |
| WO | WO2008029066 | 3/2008 |
| WO | WO 2010/118172 A1 | 10/2010 |

OTHER PUBLICATIONS

International Preliminary Report on Patentability and Written Opinion dated Oct. 20, 2011 in PCT/US2010/030296 filed on Apr. 7, 2010.

International Search Report and Written Opinion Received in PCT/US08/078087 Dated Apr. 6, 2009.

International Search Report and Written Opinion Received in PCT/US2010/030296 dated May 21, 2010.

International Search Report as mailed on Jun. 2, 2008 in PCT/US2007/088745.

PCT International Preliminary Report on Patentability in PCT/US2007/088745 dated Jun. 24, 2009.

PCT International Preliminary Report on Patentability Issued on Mar. 30, 2010 in PCT/US2008/078087.

Supplemental European Search Report dated May 10, 2011 for European Application No. 07865997.6 filed Dec. 21, 2007.

Written Opinion Received in PCT/US07/088745 dated Jul. 2, 2009.

\* cited by examiner

DISPOSABLE VITRECTOMY HANDPIECE

CROSS-REFERENCE TO RELATED APPLICATION(S)

This application claims priority to and the benefit of U.S. Provisional Patent Application Ser. No. 60/876,796, filed on Dec. 21, 2006, entitled DISPOSABLE VITRECTOMY HANDPIECE, the entire content of which is incorporated herein by reference.

FIELD OF THE INVENTION

The invention is directed to electric vitrectomy handpieces, and more particularly, the invention is directed to disposable electric vitrectomy handpieces that are small in size and light in weight.

BACKGROUND OF THE INVENTION

Vitreous is a normally clear, gel-like substance that fills the center of the eye. Certain problems affecting the eye may require a vitrectomy, or surgical removal of all or a part of the vitreous. To perform a vitrectomy, various instruments are used including a vitrectomy handpiece, a light pipe and an infusion line or port. The vitrectomy handpiece includes a cutter for removing all or a portion of the eye's vitreous. The light pipe is used as a light source, and the infusion line or port is used to replace fluid and maintain proper pressure in the eye.

Current vitrectomy handpieces have several parts, many of which can be rather expensive. For example, current vitrectomy handpieces include positional sensors that detect the position of the motor to determine when to begin aspiration. This increases the cost of manufacture, thereby increasing the cost of the device to the ultimate consumer. Moreover, while these devices are designed to be reused, the cutting tip must be replaced. Replacement cutting tips can be expensive, with a common model costing over $100.

In addition to expense, current vitrectomy handpieces include several electrical and pneumatic lines attached to the device, making the device cumbersome to operate and maneuver. Also, in order to accommodate the number of parts included in the device and the electric and pneumatic lines, the handpieces tend to be larger, contributing to the cumbersome nature of the device. Accordingly, a need exists for a less cumbersome, less expensive device that is easy to maneuver and comfortable to handle during surgery.

SUMMARY OF THE INVENTION

The invention is directed to vitrectomy handpieces that are light in weight and small in size. The light weight and small size of the device makes it easy to maneuver and comfortable to handle during surgery. In one embodiment, a vitrectomy handpiece includes an electric motor, a clutch mechanism, an oscillating drive mechanism and a cutting tip. The motor is attached to the clutch which is attached to the oscillating drive mechanism. The motor may be any electric motor suitable for use in vitrectomy handpieces. The oscillating drive mechanism may be any mechanism capable of converting rotational motion of the motor to reciprocating motion of the cutting tip.

The clutch mechanism engages the oscillating drive mechanism when the motor is running and is stationary when the motor is at rest. When the motor is at rest, the clutch mechanism allows aspiration, and when the motor is running, the clutch mechanism engages the oscillating drive mechanism, which converts the rotational motion of the clutch to reciprocating motion of the cutting tip.

In one embodiment, the vitrectomy handpiece is disposable. The disposable vitrectomy handpiece according to this embodiment is manufactured using low cost parts for assembly and manufacture. For example, an inexpensive, disposable motor may be used to manufacture a disposable vitrectomy handpiece according to an embodiment of the present invention.

The inventive vitrectomy handpieces are small in size and light in weight, enabling greater maneuverability of the device by the surgeon. In addition, the inventive vitrectomy handpieces are ergonomically designed, making the handpiece comfortable to handle during surgery.

BRIEF DESCRIPTION OF THE DRAWINGS

These and other features and advantages of the present invention will be better understood by reference to the following detailed description when considered in conjunction with the attached drawings in which.

DETAILED DESCRIPTION OF THE INVENTION

Embodiments of the present invention are directed to disposable electric vitrectomy handpieces. The handpieces are useful with, for example, 20-gauge or smaller instrumentation (e.g. 23, 25-gauge). The handpieces are small in size and cost-efficient. According to one embodiment of the invention, the small size is achieved by a disposable tool including a cutter tip integrated into the tool handle. In another embodiment, cost efficiency is achieved by a tool using plastic components and an inexpensive, disposable motor. Although described as disposable and made of plastic, it is understood that the device need not be disposable and may be made of any suitable material other than plastic, for example, metal. The drive mechanism and vitreous cutting tip have performance characteristics that are equivalent to or better than existing handpieces. Moreover, the vitrectomy handpiece maintains a substantially constant aspiration duty cycle over a range of operating speeds, such as, for example, about 3,000 to about 10,000 cpm or about 600 to about 6000 cpm.

According to one embodiment of the invention, the vitrectomy handpiece is well balanced, light in weight and has low rotational and line torque. Accordingly, the handpiece is easily maneuverable by the surgeon. In one embodiment, the vitrectomy handpiece is smaller than conventional electric handpieces, thereby facilitating mobility. According to one embodiment of the present invention, the pneumatic lines are incorporated into the handle or fully enclosed within the handle, reducing clutter and improving ease of manipulation by the surgeon. The electrical lines are much lighter than those in conventional cutters, reducing the amount of external torsion experienced by the surgeon. According to one embodiment, the electrical lines may be disposable lines that are integral with the handpiece. In another embodiment, a reusable line connecting a machine (external or otherwise) to the handpiece may be used. In yet another embodiment, an internal power supply may be used instead of electrical lines.

The vitrectomy handpiece according to embodiments of the present invention is an inexpensive surgical tool providing an electric alternative to pneumatic cutters. In some embodiments, the vitrectomy handpiece is inexpensive and disposable, eliminating the need for replacement parts. The vitrectomy handpiece may be provided as a sterile package with the cutting tip incorporated directly into the handpiece. As the handpiece may be provided fully assembled, the time needed to prepare for surgery may be significantly reduced. Also, with disposable designs, the surgeon may bill directly for the tools used in the procedure, which option is not available when using a reusable vitrectomy tool with replacement parts.

Figure 1:
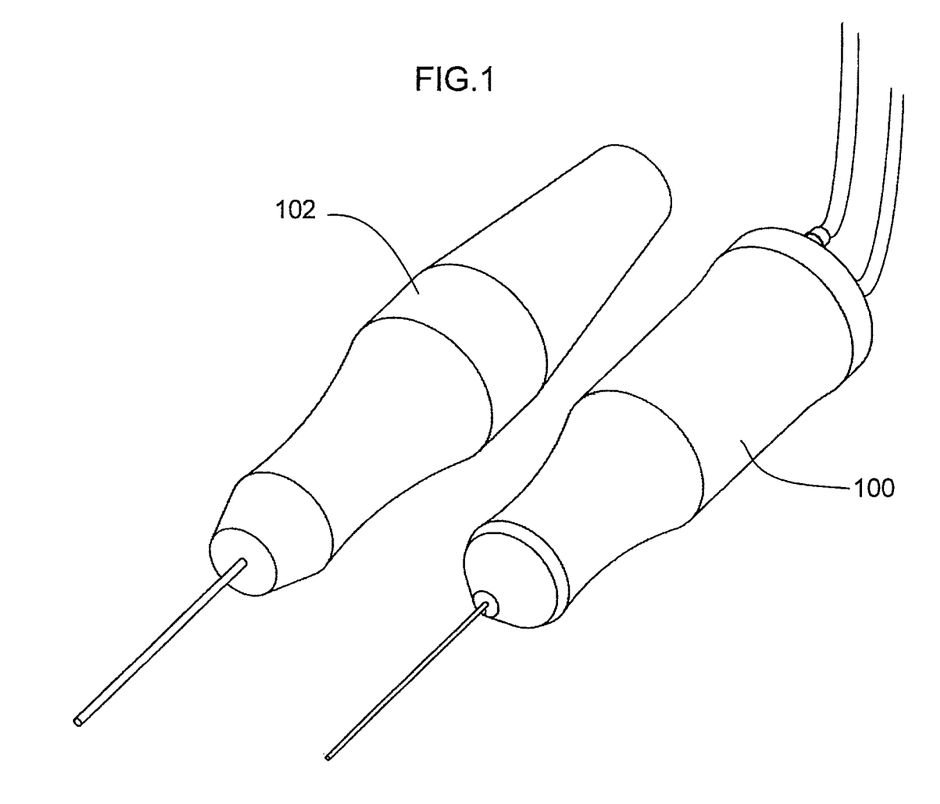
FIG. 1 is a photograph comparing a vitrectomy handpiece according to an embodiment of the present invention with a vitrectomy handpiece according to the prior art.

Many considerations are taken into account when designing a vitrectomy handpiece. Some such considerations include cost, size, low noise and vibration, aspiration duty cycle and traction. In the disposable embodiments of the present invention, cost is a concern. To reduce cost, the components of the vitrectomy handpiece may be manufactured in high volume, using low cost techniques such as injection molding, CNC machining, overmolding, deep drawing, EDM, and the like. Additionally, reducing part count and handpiece size significantly reduces the total cost of the handpiece. To that end, integrating the tip into the handpiece not only lowers part count, but also reduces the overall size of the unit, yielding a size comparable to or smaller than existing vitrectomy handpieces (e.g. the Alcon Innovit). As shown in FIG. 1, a vitrectomy handpiece 100 according to one embodiment of the present invention is smaller than the Alcon Innovit handpiece 102.

Another consideration in designing vitrectomy handpieces is minimizing noise and vibration. High levels of noise and vibration adversely affect maneuverability of the tool during surgery, and makes it difficult for the surgeon to make precise cuts. To minimize noise and vibration, the drive mechanism according to one embodiment has balanced components, smooth transitions as the cutter is extended and retracted, and good alignment of the drive components. These characteristics increase the precision of the internal components and therefore impact the method of manufacture. In one embodiment of the invention, to reduce noise and vibration, the vitrectomy handpiece has an invariable cutting duty cycle at a wide range of operating speeds. In addition, to reduce traction in comparison to existing electric cutters, a vitrectomy handpiece according to one embodiment of the present invention has a maximum cut speed targeted between about 6000 cpm and about 10,000 cpm. Another way to dampen vibration includes providing a rubber, foam, silicon, or other like tube around the motor.

Figure 2A:
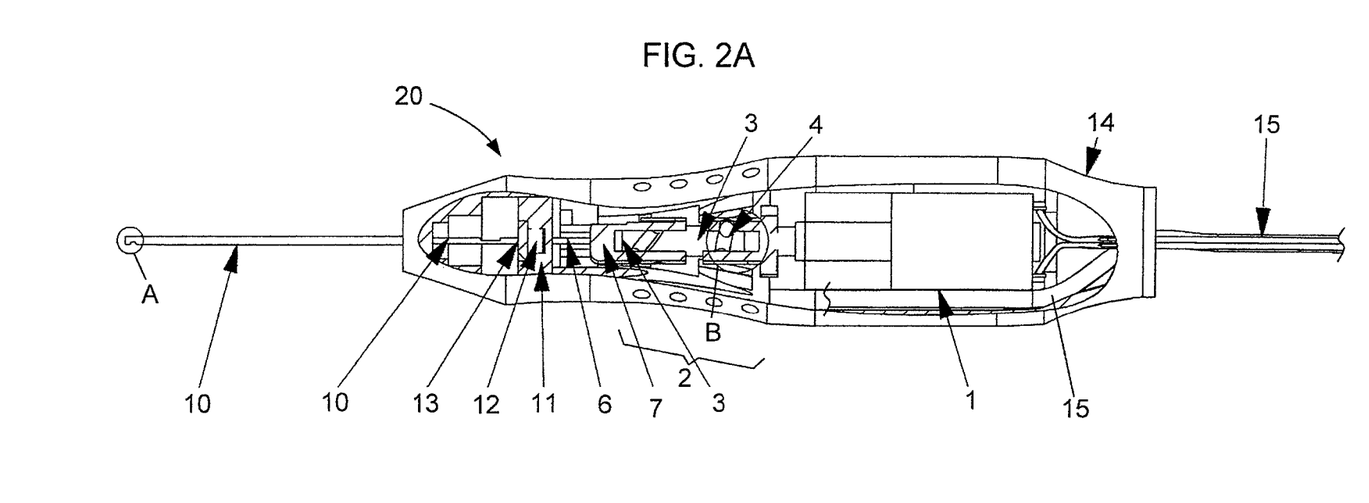
FIG. 2A is a partial cross-sectional view of a vitrectomy handpiece according to one embodiment of the present invention.
Figure 2B:
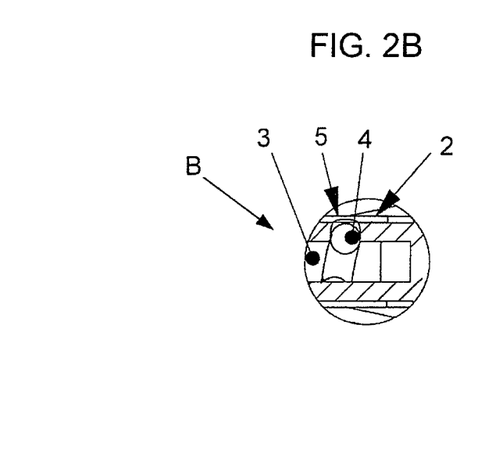
FIG. 2B is an exploded view of area B in FIG. 2A.
Figure 2C:
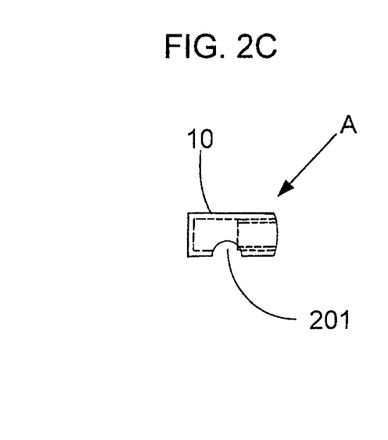
FIG. 2C is an exploded view of area C in FIG. 2A.
Figure 3:
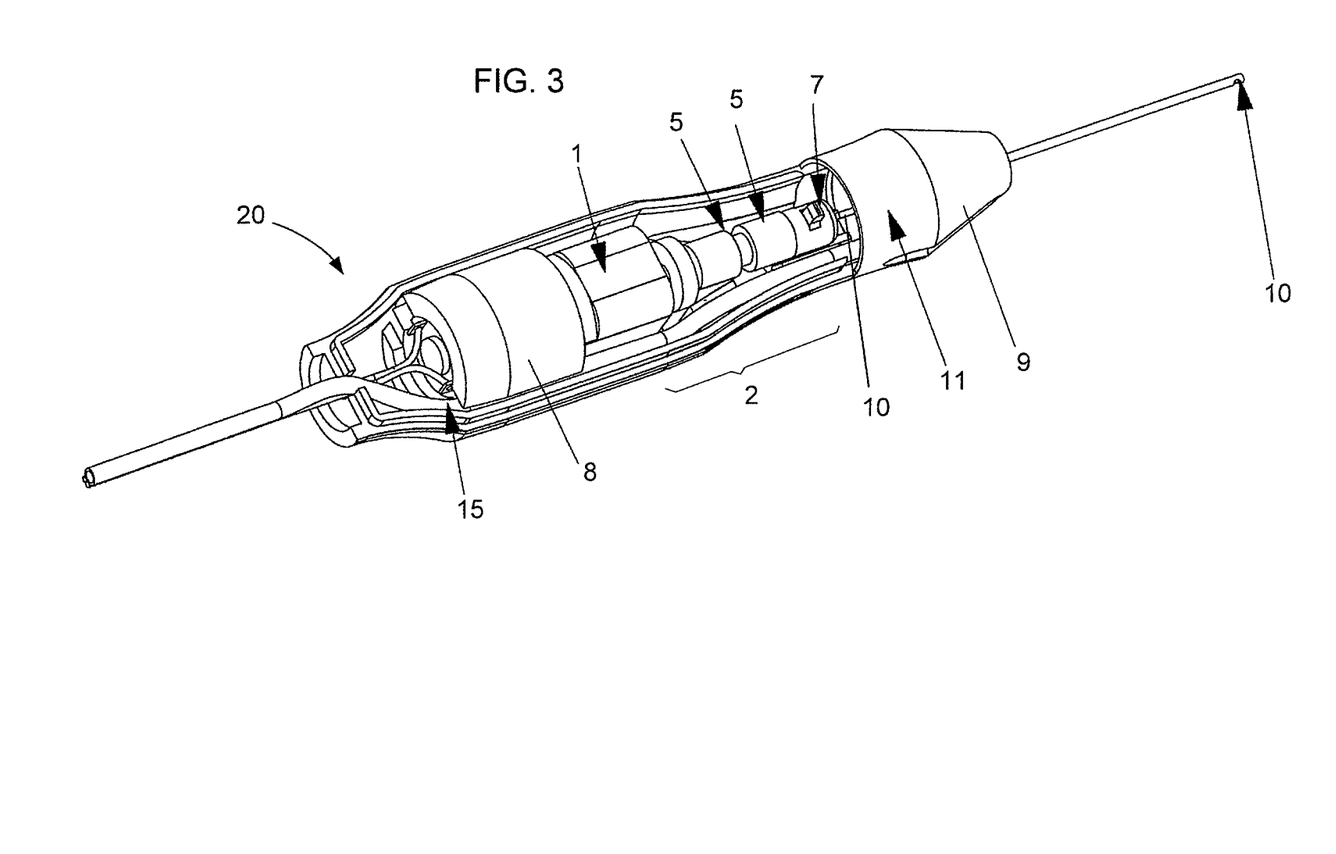
FIG. 3 is a partially cut-away side view of a vitrectomy handpiece according to one embodiment of the present invention.
Figure 4:
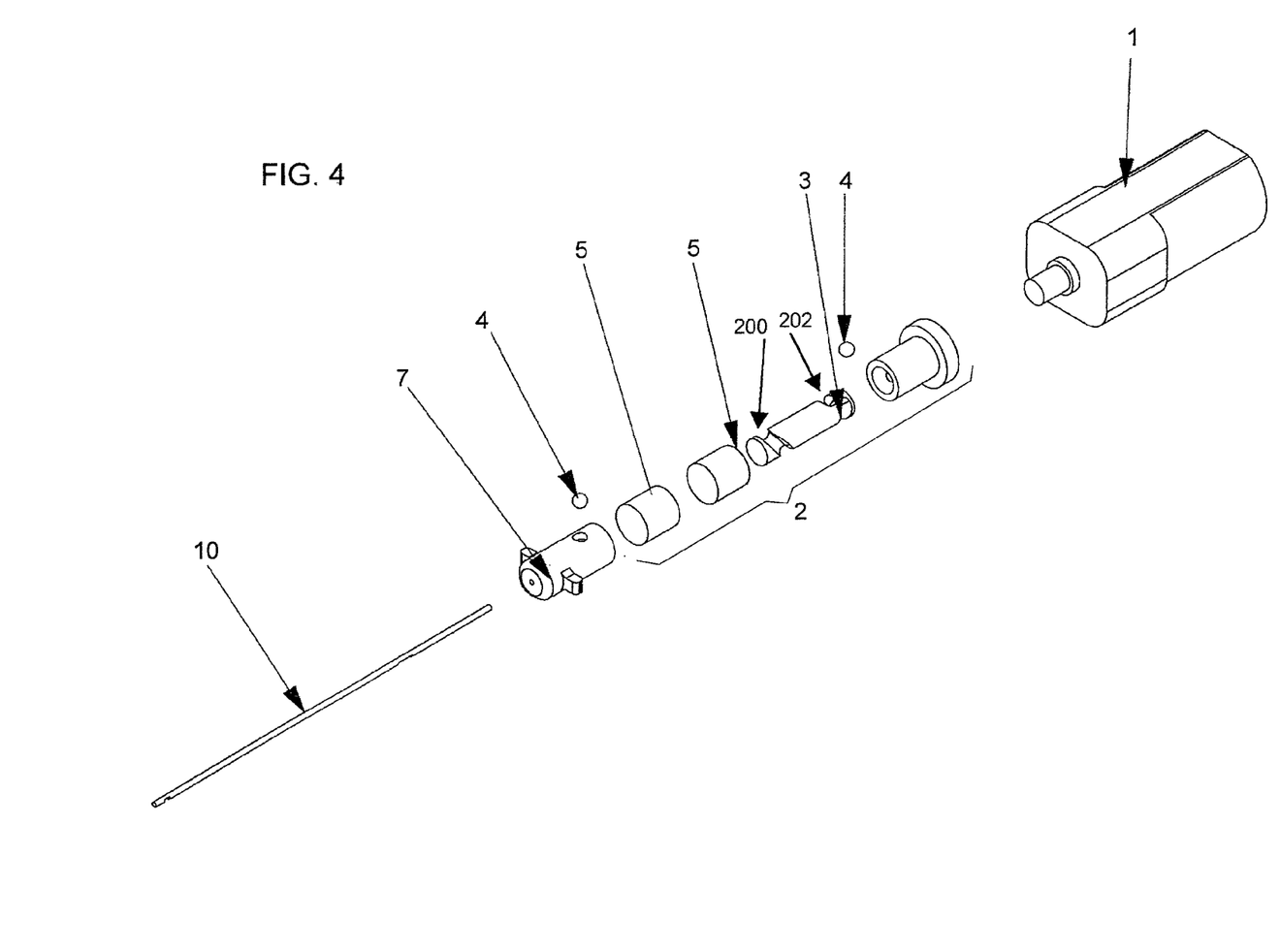
FIG. 4 is an exploded schematic view of a motor, clutch mechanism, drive mechanism and cutting tip of a vitrectomy handpiece according to one embodiment of the present invention.
Figures 5A, 5B, 5C, 5D, 5E:
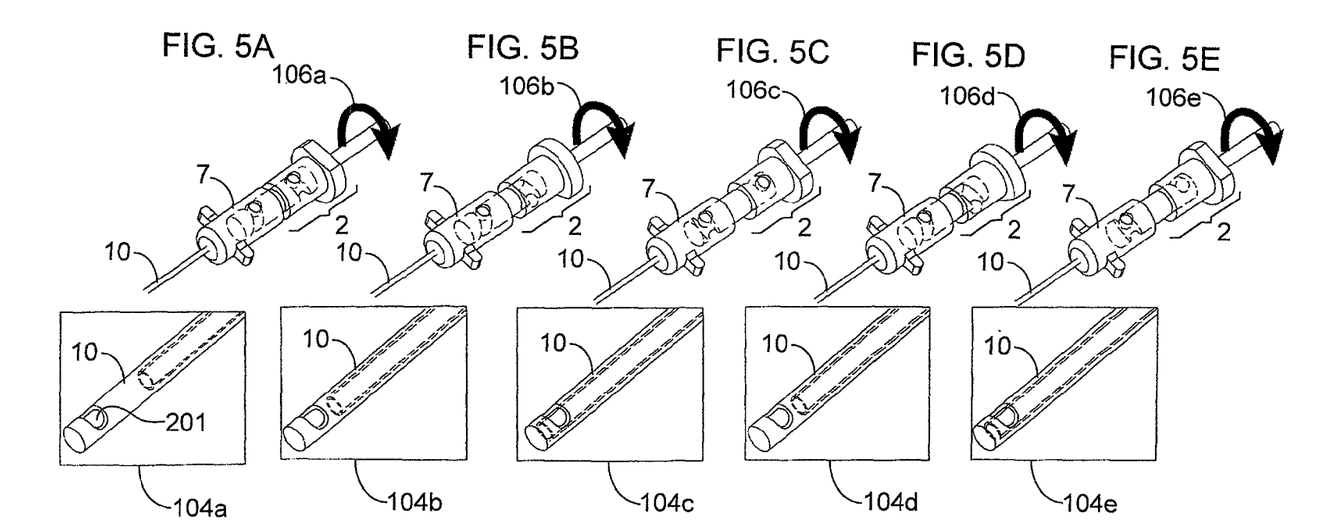
FIGS. 5A through 5E are schematic diagrams depicting the motion of a clutch mechanism and drive mechanism during a cutting process of a vitrectomy handpiece according to one embodiment of the present invention.

FIGS. 2 through 4 are detailed diagrams of various vitrectomy cutters 20 according to certain embodiments of the present invention. According to the illustrated embodiment, the cutter 20 includes a motor 1, a clutch mechanism 2, an oscillating drive mechanism 7, and a cutter tip 10 mounted inside a handle 14. The handle 14 is used to mount and align the various components, provide ergonomic design for the surgeon, and route aspiration lines. In one embodiment, the cutter tip 10 is directly integrated into the handle 14. This integration helps reduce complexity and part count by eliminating the interface components between the tip and the handle.

According to one embodiment, the motor 1 is attached to the clutch 2. The clutch expands to engage the oscillating drive 7 and cutter tip 10 when the motor 1 is operational and retracts to allow aspiration via the aspiration line 15 when the motor 1 is at rest. The oscillating drive 7 converts the motor 1 rotation into a smooth reciprocating motion of the cutter tip 10. The oscillating drive may be any device capable of converting rotary to oscillating linear motion, such as, for example, a crankshaft.

Although the clutch is described as allowing aspiration when the motor is off, it is understood that the vitrectomy handpiece aspirates during the cutting process as well. During a cutting process, the aspiration port 201 opens and closes repeatedly as the cutter is extended and retracted. Aspiration occurs through the open aspiration port 201 throughout the cutting process. However, in conventional vitrectomy handpieces, when the motor is turned off, the cutter may either be extended to close the aspiration port or retracted to open the aspiration port, and the position of the cutter is random depending on when during the cutting process the motor is turned off. In contrast, according to one embodiment of the present invention, the clutch mechanism 2 retracts the cutter when the motor is turned off, ensuring that the aspiration port is open when the motor is turned off.

The actuation of the clutch 2 may be achieved in different ways. For example, the clutch 2 may retract by reversing the motor 1. In this embodiment, the motor automatically runs in reverse for a short period when the motor turns off. The reverse motion of the motor causes the clutch to retract, thereby allowing aspiration via the aspiration line 15.

In an alternative embodiment, a spring return may be employed so that when the motor 1 is off, the clutch 2 retracts. This alternative clutch mechanism may be used in conjunction with a spring to retract the clutch and open the aspiration port when the cutter is turned off. The design of the previous embodiment uses slow reversed motion of the motor to open the aspiration port. A design with light springs allows the clutch to retract without any reverse motion of the motor. This helps simplify the control required for the tool, but may increase the complexity and thus the overall cost of the unit.

The clutch mechanism 2 is used to engage the cutter tip 10 when the handpiece is operated, and allow aspiration when the cutter is stationary. Existing electric vitrectomy handpieces use a positional sensor to monitor the position of the motor to determine when to initiate aspiration. In such conventional handpieces, the motor is rotated to a position where the aspiration port is open when the cutter is at rest. This allows full aspiration through the tip of the instrument when it is not being used to cut. However, the vitrectomy handpieces according to embodiments of the present invention use clutching mechanisms to reduce cost and part count, as well as to improve maneuverability of the instrument. The clutch eliminates the need for a positional sensor, which not only reduces overall unit cost, but also reduces the number of electrical lines attached to the cutter. The smaller cord attached to the cutter makes it easier to maneuver by the surgeon. This also results in less line torque.

According to one embodiment, the clutch mechanism 2 includes two components that rotate relative to each other when torque is transmitted across them. With reference to FIGS. 2B and 4, a groove 200 is cut in the first component 3. The groove may have any suitable profile, and in one embodiment, is half of a sinusoidal groove. The second component 5 captivates a ball 4 which rides in the groove 200. When the motor is turned on, torque is transmitted across the two components of the clutch mechanism, causing them to rotate relative to one another. As the two components rotate with respect to one another, the ball rolls or slides along the groove, causing the two components to expand or contract. When the ball reaches the end of the groove, it comes to a hard stop. Subsequently, both components of the clutch rotate together, transmitting rotary motion to the oscillating drive mechanism 7. The oscillating drive mechanism 7 converts the rotational motion into smooth reciprocating linear motion of the cutter.

As an alternative to the groove 200, the clutch may include a pin riding on a cam (not shown), or the like. Regardless of the embodiment, however, the clutch/cam may be implemented as a single component to reduce cost, or be separated into two elements.

FIGS. 5A to 5E illustrate portions of the oscillating drive mechanism 7 and clutch mechanism 2 during a cutting process. The cutter tip 10 at each step is shown in a box 104*a*-104*e* below the drive and clutch mechanisms. The motor provides rotary motion which is depicted by curved arrows 106*a*-106*e*. At the position illustrated in FIG. 5A, the cutter is starting from rest and beginning to cut. In this position, both the clutch 2 and cutter tip 10 are retracted and the aspiration port 201 is open. As the motor begins to rotate, the clutch expands until it reaches the engaged position (the position illustrated in FIG. 5B). The clutch remains engaged as long as the cutter is cutting (the positions illustrated in FIGS. 5B through 5E). When the clutch is engaged, the oscillating drive mechanism 7 travels enough to move the cutter across the aspiration port 201. At the positions illustrated in FIGS. 5C through 5E, the clutch 2 is engaged, and the oscillating drive 7 is opening and closing the cutter. At the position illustrated in FIG. 5C, the oscillating drive mechanism 7 closes the cutter for the first cut. The cutter is then open at the position illustrated in FIG. 5D and closed again at the position illustrated in FIG. 5E.

The motor may be any suitable motor known in the art, and in one embodiment, may be a disposable motor. Using disposable motors, which are generally less expensive than their reusable counterparts, reduces not only the cost of the motor but also the cost of the vitrectomy handpiece. A disposable design also allows use of plastic components and gearing. When purchased in high volumes, high quality, miniature DC motors with gearing may cost about $30 or more. Although such disposable motors typically have shorter lifespans than their non-disposable counterparts, because the motor is disposable, the lifespan requirement is reduced compared to non-disposable motors. For a disposable instrument, the longevity of the motor is not as stringent, and more cost effective motors can be considered.

Small DC motors generally require gearing due to the output speed range (which may be about 600 cpm to about 6000 cpm), and the high torque needed (stall torque of about 7 mNm). Typical small DC motors run at speeds above about 5000 rpm, with many of them having free running speeds above about 15000 rpm. Pre-geared motors meet the shaft speed and torque requirements, but they increase both price and footprint.

Gearing small DC motors is another option to optimize overall cost. One method of achieving this includes using a motor with relatively high torque (stall torque of about 2 to about 3 mNm) and relatively low free running speed (about 10,000 rpm), and incorporating minimal gearing to obtain the desired speed. Gearing may include a frictional drive, a single set of spur gears, a plastic planetary gear, or a harmonic drive. Typically, a motor with high torque and low free running speed will be larger than the faster running lower torque models. The cost of the different motors will be similar. To reduce the footprint of the vitrectomy handpiece, a smaller motor may be used with gearing similar to a harmonic drive. This type of gearing has a relatively low part count and allows for high reduction ratios in a small space. Ultimately, the gearing decision will be a cost trade-off analysis of the various designs and projected cost of manufacture.

According to one embodiment, the handle 14 of the vitrectomy handpiece not only holds the motor 1 and drive mechanisms 2 and 7, but also the aspiration line 15. Routing the aspiration line through the handle reduces clutter and improves maneuverability of the tool. According to one embodiment, the aspiration line begins inside the handle and is routed to a port in the back of the handle. A small electrical line is bundled with the aspiration line at the back of the handle in a single cord. The cord (including the aspiration line and electrical line) may be integrated with the handpiece to form a single component.

Figure 6:
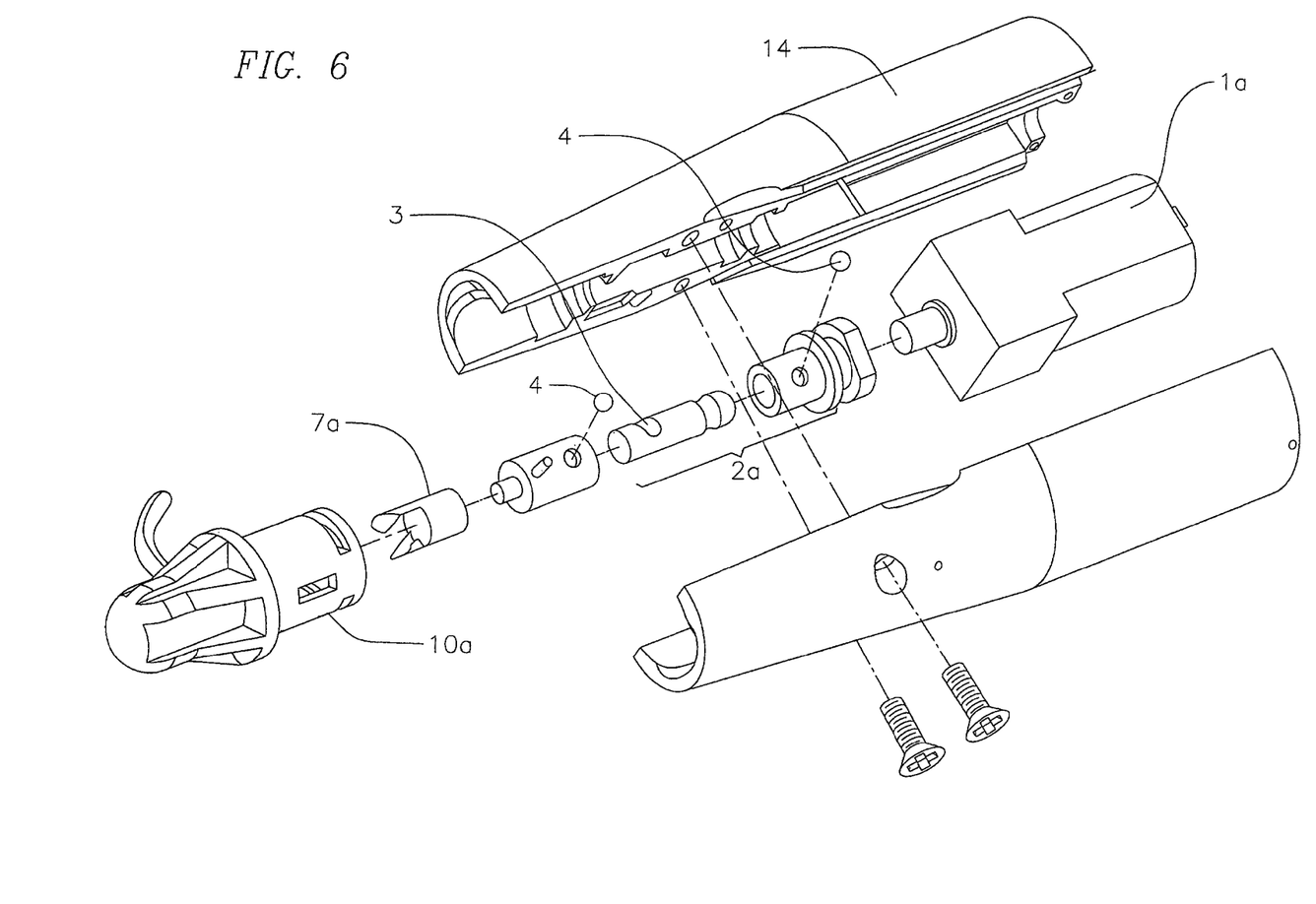
FIG. 6 is an exploded view of a vitrectomy handpiece according to one embodiment of the present invention.

According to other embodiments of the invention, the vitrectomy handpiece interfaces with existing cutter tips 10*a* as is illustrated in FIG. 6. As shown in FIG. 6, a vitrectomy handpiece according to one embodiment of the present invention including a motor 1*a*, clutch mechanism 2*a* and oscillating drive mechanism 7*a* interfaces with a commercially available cutter tip 10*a*.

According to another embodiment of the invention, as shown in FIGS. 2-3, the vitrectomy handpiece incorporates the cutter tip 10 into the handle 14 and the aspiration line 15 is routed through the handle 14. This configuration eliminates the need for an externally connected aspiration line, and thus improves maneuverability of the handpiece. In one embodiment, the aspiration line 15 may be routed around the motor, as shown in FIGS. 2A and 3. In addition to yielding all the benefits of routing the aspiration line inside the handle, this configuration cools the motor, keeping it from overheating, as the aspiration fluid runs across the motor 1 through the aspiration line 15. Such a configuration also helps dampen vibration.

In another embodiment of the invention, a speed sensor may be incorporated into the handpiece for sensing speed, proper operation of the handpiece, and the like. The speed sensor may include a sensor and a magnet. In another embodiment, instead of using a sensor, speed may be measured by measuring a current ripple as the motor rotates, measuring current/voltage curves and extrapolating speed based on the measured data, and the like.

According to another embodiment of the invention, stall of the handpiece may be detected by looking at the current draw to find failure.

In one embodiment, tabs may be integrated into the handle to prevent rotation of the tip by the drive mechanism.

According to another embodiment, a seal is provided. As shown in FIGS. 2 and 3, the seal may include a seal housing 11, an o-ring or diaphragm seal 12 and a seal retainer 13.

To be viable alternatives to pneumatic cutters, the cost of the inventive vitrectomy handpieces should be comparable to or less than existing cutter tips. To reduce cost, according to one embodiment, all components in the design are made of plastic. However, it is understood that the present invention is not limited to plastic, and that any other material that lends itself to high volume and low cost manufacturing techniques may be employed in lieu of or in addition to plastic.

The components of the vitrectomy handpiece may be manufactured by molding or CNC techniques conventional in the art. Molding may have a higher upfront tooling cost, but provides low unit cost unit when purchased in large volumes. CNC parts provide improved component tolerances, but unit cost is increased when purchased in large volumes. If high tolerance is required for the clutch mechanism, molding may be used in conjunction with a CNC finishing pass (bored hole or a sinusoidal cam cut). A study on performance versus part tolerance may be evaluated to understand the exact specifications for the mold and/or CNC parts.

Optimal gearing of the handpiece may be achieved by testing traction and cutting efficiency as a function of cutter rate. This testing will allow optimization of top speed. With this information, the gearing of the handpiece may be modified for operation at an optimal cut rate.

Although this invention has been described with respect to certain specific embodiments, those skilled in the art will have no difficulty devising variations to the described embodiments which in no way depart from the scope and spirit of the present invention. For example, although the present invention has been described with respect to electric vitrectomy handpieces, those of ordinary skill in the art will appreciate that the described designs may also apply to pneumatic vitrectomy handpieces. Furthermore, to those skilled in the various arts, the invention itself herein will suggest solutions to other tasks and adaptations for other applications. It is Applicants' intention to cover all such uses of the invention and those changes and modifications which could be made to the embodiments of the invention herein chosen for the purpose of disclosure without departing from the spirit and scope of the invention. Thus, the present embodiments of the invention should be considered in all respects as illustrative and not restrictive.

What is claimed is:

1. A vitreous cutter comprising:
   a motor configured to provide rotary motion;
   a handle;
   a cutter tip;
   an aspiration line; and
   a clutch coupled to the motor and the cutter tip, the clutch configured to:
   engage and linearly reciprocate the cutter tip when the motor is activated, and
   retract the cutter tip through reverse operation of the motor to open an aspiration port when the motor is at rest.

2. The vitreous cutter according to claim 1, wherein the clutch comprises a component including a groove.

3. The vitreous cutter according to claim 2, wherein the groove is a sinusoidal groove.

4. The vitreous cutter according to claim 1, wherein the motor is a disposable motor.

5. The vitreous cutter according to claim 1, wherein the cutter tip is integrated into a handle.

6. The vitreous cutter according to claim 1, wherein the aspiration line is routed through a handle.

7. The vitreous cutter according to claim 6, wherein the aspiration line is routed around the motor.

8. The vitreous cutter according to claim 1, further comprising a means for sensing a speed of the cutter tip.

9. The vitreous cutter according to claim 8, wherein the means for sensing the speed of the cutter tip comprises a sensor and a magnet.

10. The vitreous cutter according to claim 1, further comprising a means for detecting motor failure by monitoring high current draw.

11. The vitreous cutter according to claim 1, further comprising an oscillating drive mechanism configured to convert the rotary motion of the motor to oscillatory linear motion.

12. The vitreous cutter according to claim 1, further comprising a means for reducing vibration in a handle.

13. The vitreous cutter according to claim 12, wherein the means for reducing vibration in the handle comprises a rubber or foam tube surrounding the motor, wherein the tube is compressed against the motor by the handle.

14. The vitreous cutter according to claim 12, wherein the means for reducing vibration in the handle comprises a compressed silicone tubing surrounding the motor.

15. The vitreous cutter according to claim 1, further comprising a means for preventing heat transfer from the motor to a handle.

16. The vitreous cutter according to claim 15, wherein the means for preventing heat transfer from the motor to the handle comprises an insulating material surrounding the motor.

* * * * *